(12) United States Patent
Ramin et al.

(10) Patent No.: US 6,203,806 B1
(45) Date of Patent: Mar. 20, 2001

(54) COSMETIC VARNISH COMPOSITION BASED ON NITROCELLULOSE AND COMPRISING A STABILIZER

(75) Inventors: Roland Ramin, Paris (FR); Chris Frankfurt, Old Bridge, NJ (US)

(73) Assignee: L'Oreal S,A., Paris (FR)

( * ) Notice: Subject to any disclaimer, the term of this patent is extended or adjusted under 35 U.S.C. 154(b) by 0 days.

(21) Appl. No.: 09/219,926

(22) Filed: Dec. 23, 1998

(30) Foreign Application Priority Data

Dec. 29, 1997 (FR) .................................................. 97 16626

(51) Int. Cl.⁷ .............................. A61K 6/00; A61K 7/00; A61K 7/04
(52) U.S. Cl. .............................................. 424/401; 424/61
(58) Field of Search ....................... 424/401, 61

(56) References Cited

U.S. PATENT DOCUMENTS

| 5,102,654 | 4/1992 | Castrogiovanni et al. | ............ 424/61 |
|---|---|---|---|
| 5,254,161 | * 10/1993 | DeVido et al. | ....................... 106/170 |
| 5,580,548 | * 12/1996 | Mellul et al. | ............................ 424/61 |

FOREIGN PATENT DOCUMENTS

| 2 679 445 | 1/1993 | (FR) . |
| 2 737 114 | 1/1997 | (FR) . |

OTHER PUBLICATIONS

English Language Derwent Abstract of FR 2 737 114.

* cited by examiner

*Primary Examiner*—Thurman K. Page
*Assistant Examiner*—S. Howard
(74) *Attorney, Agent, or Firm*—Finnegan, Henderson, Farabow, Garrett & Dunner

(57) ABSTRACT

Cosmetic varnish composition. At least one solvent, at least one nitrocellulose, at least one plasticizer, at least one resin, at least one otherwise unstable compound, preferably chosen from amino- and amido-functional compounds, and at least one stabilizer chosen from N-chlorosuccinimide and boric acid. The stabilizer is present in an amount effective to stabilize the at least one otherwise unstable compound. The composition is used for making nail varnish, make-up, or treatment varnish which is highly stable over time.

38 Claims, No Drawings

COSMETIC VARNISH COMPOSITION BASED ON NITROCELLULOSE AND COMPRISING A STABILIZER

The present invention relates to a nitrocellulose-based, i.e., nitrocellulose-containing, cosmetic varnish composition which is coloured or colourless, and in addition to the usual ingredients, comprises at least one otherwise unstable compound having at least one amine or amide function and a stabilizer for the said otherwise unstable compound.

It has been observed that in nitrocellulose-based cosmetic varnish compositions certain compounds such as dyes, pigments, and other compounds used to treat nail keratin breakdown over a period of time, especially when these compounds possess at least one amine or amide function.

Representative amino- or amido-functional dyes susceptible to breakdown in nitrocellulose-based varnish compositions include D&C Red No. 33, D&C Green No. 6, D&C Violet No. 2 and D&C Green No. 5, and other organic pigments such as D&C Red No. 33 aluminium lakes and guanine or 2-amino-6-hydroxypurine, the latter being known to impart a pearly lustre to varnishes due to its high refractive index.

Representative amino- or amido-functional active substances used to treat nail keratin that are susceptible to breakdown in nitrocellulose-based varnish compositions are, in particular, D-panthenol, calcium panthenate and 2-oleoylaminooctadecane-1,3-diol.

Other active substances intended for treatment of the nails, especially in the case of children, may also be susceptible to breakdown. A representative compound is N-[2-[(2,6-dimethylphenyl)amino]-2-oxoethyl]-N,N-diethylbenzene-methanaminium benzoate, or BITREX®, which is known as an agent for treating onychophagy, due to its very bitter taste.

We have discovered that certain compounds can stabilize dyes and/or pigments and the active nail treatment substances, such as the compounds defined above and, therefore, prevent or reduce the deterioration of colour or loss of activity of nitrocellulose-based cosmetic varnish compositions.

In one aspect, therefore, the present invention provides, as a novel industrial product, a nitrocellulose-based cosmetic varnish composition comprising at least one solvent, at least one nitrocellulose, at least one plasticizer, at least one resin, at least one otherwise unstable compound, preferably chosen from amino- and amido-functional compounds, and at least one stabilizer chosen from N-chlorosuccinimide and boric acid, the least one stabilizer being present in an amount effective to stabilize the at least one otherwise unstable compound.

According to the invention, the percentage of stabilizer preferably ranges from 0.7 to 5%, more preferably from 2 to 4%, by weight relative to the weight of nitrocellulose.

In the cosmetic varnish compositions according to the present invention, the nitrocellulose is generally present in a film-forming amount. Preferably, that amount represents from 5 to 20% by weight relative to the total weight of the cosmetic varnish composition and more preferably from 10 to 16% by weight relative to the total weight of the cosmetic varnish composition.

Particularly preferred nitrocelluloses include the "RS" or "SS" type and, even more particularly, the nitrocellulose type ¼ second RS, nitrocellulose type ½ second RS, nitrocellulose type ½ second SS and nitrocellulose type ¾ second RS.

According to the invention, the plasticizer represents in the varnish composition from 2 to 12%, preferably from 5 to 10%, by weight relative to the total weight of the cosmetic varnish composition.

The plasticizers make it possible to vary the flexibility of the film without weakening its physical strength.

Representative plasticizers which can be used in the cosmetic varnish compositions according to the invention include tricresyl phosphate, benzyl benzoate, tributyl phosphate, butyl acetylricinoleate, glyceryl acetylricinoleate, dibutyl phthalate, butyl glycolate, dioctyl phthalate, butyl stearate, tributoxyethyl phosphate, triphenyl phosphate, triethyl citrate, tributyl citrate, tributyl acetylcitrate, tri-2-ethylhexyl acetylcitrate, dibutyl tartrate, dimethoxyethyl phthalate, diisobutyl phthalate, diamyl pthalate, camphor, glycerol triacetate, and mixtures thereof.

According to the invention, the cosmetic varnish compositions include a resin, which generally represents from 0.5 to 15%, preferably from 5 to 10%, by weight relative to the total weight of the cosmetic varnish composition.

Among the many resins which can be used it is preferred to employ, in accordance with the invention, resins of the arylsulphonamide-formaldehyde or arylsulphonamide-epoxy type, especially the toluenesulphonamide-formaldehyde resin which is better known under the tradenames "Santolite MHP®", "Santolite MS 80%®" and "Ketjenflex MS 80®", or alkyd resins, such as those sold by the Dainippon company under the name "Beckosol ODE 230-70®".

These resins not only increase the film-forming power but at the same time enhance the gloss and the adhesion properties.

According to the invention, the solvent system of the varnish composition, i.e., the at least one solvent, represents from 55 to 90% by weight relative to the total weight of the varnish composition.

This solvent system comprises a mixture of various volatile organic solvents, preferably designed to provide relatively short drying times.

Preferred solvents are methyl acetate, ethyl acetate, isopropyl acetate, butyl acetate, amyl acetate, 2-methoxyethyl acetate, acetone, methyl ethyl ketone and methyl isobutyl ketone.

The composition may additionally contain a diluent, which is preferably a saturated linear or branched hydrocarbon, such as hexanes or octanes, or else an aromatic hydrocarbon, such as toluene or xylene, preferably in an amount ranging from 10 to 35% relative to the total weight of the cosmetic varnish composition.

The solvent system can additionally include volatile solvents such as ethanol, n-propanol, isopropanol, n-butanol or mixtures thereof.

Coloured cosmetic varnish compositions according to the invention may additionally comprise other dyes and/or pigments, either organic or inorganic.

Preferred organic pigments include D&C Red Nos. 10, 11, 12 and 13, D&C Red No. 7, D&C Red Nos. 5 and 6 and D&C Red No. 34, as well as lakes such as D&C Yellow No. 5 lake and D&C Red No. 2 lake.

Preferred inorganic pigments include titanium dioxide, bismuth oxychloride, brown iron oxide, and red iron oxides.

Preferably, the dyes and/or pigments are present in the cosmetic varnish compositions according to the invention in amounts ranging from 0.01 to 2% by weight relative to the total weight of the varnish composition.

To prevent sedimentation of the pigments, certain thixotropic agents may be employed, such as, for example, "Bentone 27®" or "Bentone 38®".

The cosmetic varnish compositions according to the present invention may also comprise conventional adjuvants, such as UVA and/or UVB screening agents, which are benzophenone derivatives and ethyl 2-cyano-3,3-diphenylacrylate, dispersants and wetting agents, dulling agents, adhesion agents, spreading agents, rheological agents such as pyrogenic silicas, antioxidants, preservatives, thickeners and nail hardeners.

A number of examples of varnish compositions according to the invention will now be given by way of illustration.

VARNISH EXAMPLES

| EXAMPLE 1: Coloured nail varnish | |
|---|---|
| Nitrocellulose | 20 g |
| Tributyl acetylcitrate | 6 g |
| Toluenesulphonamide-formaldehyde resin | 4 g |
| N-Chlorosuccinimide | 0.4 g |
| D&C Red No. 33 | 0.001 g |
| Other pigments and dyes | 1 g |
| (Ethyl acetate, butyl acetate, acetone 20/60/20) | q.s. 100 g |

This varnish exhibits good colouring stability over time.

In the absence of N-chlorosuccinimide, a rapid alteration in the colouring of the varnish is observed.

| EXAMPLE 2: Nail care varnish | |
|---|---|
| Nitrocellulose | 20 g |
| Tributyl acetylcitrate | 6 g |
| Toluenesulphonamide-formaldehyde resin | 4 g |
| Boric acid (10% strength aqueous solution) | 0.4 g |
| Clay (Bentone 27 ®) | 1 g |
| Isopropyl alcohol | 6 g |
| Organic pigments | 1 g |
| D-Panthenol | 0.5 g |
| (Ethyl acetate, butyl acetate 50/50) | q.s. 100 g |

In the absence of boric acid, analysis of this varnish shows severe breakdown of the D-panthenol.

What is claimed is:

1. A cosmetic varnish composition comprising at least one solvent, at least one nitrocellulose, at least one plasticizer, at least one resin, at least one otherwise unstable compound chosen from amino- and amido-functional compounds, and at least one stabilizer chosen from N-chlorosuccinimide and boric acid, said at least one stabilizer being present in an amount effective to stabilize said at least one otherwise unstable compound.

2. The composition of claim 1, wherein said at least one nitrocellulose is chosen from "RS" and "SS" nitrocelluloses.

3. The composition of claim 2, wherein said at least one nitrocellulose is chosen from nitrocellulose ¼ second RS, nitrocellulose ½ second RS, nitrocellulose ½ second SS and nitrocellulose ¾ second RS.

4. The composition of claim 1, wherein said at least one nitrocellulose is present in an amount ranging from 5 to 20% by weight relative to the total weight of the composition.

5. The composition of claim 4, wherein said at least one nitrocellulose is present in an amount ranging from 10 to 16% by weight relative to the total weight of the composition.

6. The composition of claim 1, wherein said at least one stabilizer is present in an amount ranging from 0.7 to 5% by weight relative to the weight of said at least one nitrocellulose.

7. The composition of claim 6, wherein said at least one stabilizer is present in an amount ranging from 2 to 4% by weight relative to the weight of said at least one nitrocellulose.

8. The composition of claim 1, wherein said at least one solvent comprises at least one organic solvent.

9. The composition of claim 8, wherein said at least one organic solvent is chosen from methyl acetate, ethyl acetate, isopropyl acetate, butyl acetate, amyl acetate, 2-methoxyethyl acetate, acetone, methyl ethyl ketone, and methyl isobutyl ketone.

10. The composition of claim 1, wherein said at least one solvent is present in an amount ranging from 55 to 90% by weight relative to the total weight of the composition.

11. The composition of claim 1, wherein said composition additionally comprises at least one diluent.

12. The composition of claim 11, wherein said at least one diluent is chosen from saturated linear hydrocarbons, saturated branched hydrocarbons, and aromatic hydrocarbons.

13. The composition of claim 12, wherein said linear and branched hydrocarbons are chosen from hexanes and octanes.

14. The composition of claim 12, wherein said aromatic hydrocarbons are chosen from toluene and xylene.

15. The composition of claim 11, wherein said at least one diluent is present in an amount ranging from 10 to 35% weight relative to the total weight of the composition.

16. The composition of claim 1, wherein said at least one solvent comprises at least one volatile solvent.

17. The composition of claim 16, wherein said at least one volatile solvent is chosen from ethanol, n-propanol, isopropanol, and n-butanol.

18. The composition of claim 1, wherein said at least one plasticizer is chosen from tricresyl phosphate, benzyl benzoate, tributyl phosphate, butyl acetylricinoleate, glyceryl acetylricinoleate, dibutyl phthalate, butyl glycolate, dioctyl phthalate, butyl stearate, tributoxyethyl phosphate, triphenyl phosphate, triethyl citrate, tributyl citrate, tributyl acetylcitrate, tri-2-ethylhexyl acetylcitrate, dibutyl tartrate, dimethoxyethyl phthalate, diisobutyl phthalate, diamyl pthalate, camphor, and glycerol triacetate.

19. The composition of claim 1, wherein said at least one plasticizer is present in an amount ranging from 2 to 12% by weight relative to the total weight of the composition.

20. The composition of claim 19, wherein said at least one plasticizer is present in an amount ranging from 5 to 10% by weight relative to the total weight of the composition.

21. The composition of claim 1, wherein said at least one resin is chosen from arylsulphonamide-formaldehyde resins, arylsulphonamide-epoxy resins, toluenesulphonamide-formaldehyde resins, and alkyd resins.

22. The composition of claim 1, wherein said at least one resin is present in an amount ranging from 0.5 to 15% by weight relative to the total weight of the composition.

23. The composition of claim 22, wherein said at least one resin is present in an amount ranging from 5 to 10% by weight relative to the total weight of the composition.

24. The composition of claim 1, wherein said at least one otherwise unstable compound is chosen from dyes, organic pigments, and inorganic pigments.

25. The composition of claim 24, wherein said at least one unstable compound is chosen from organic pigments chosen from D&C Red No. 33, D&C Green No. 6, D&C Violet No. 2, D&C Green No. 5, D&C Red No. 33 aluminium lake, and guanine.

26. The composition of claim 24, wherein said at least one unstable compound is chosen from organic pigments chosen from D&C Red Nos. 5, 6, 7, 12, 13, and 34, D&C Yellow No. 5 lake, and D&C Red No. 2 lake.

27. The composition of claim 24, wherein said inorganic pigments are chosen from titanium dioxide, bismuth oxychloride, brown iron oxide, and red iron oxides.

28. The composition of claim 24, wherein said at least one otherwise unstable compound is present in an amount ranging from 0.01 to 2% by weight relative to the total weight of the composition.

29. The composition of claim 1, wherein said at least one otherwise unstable compound is chosen from D-panthenol, calcium panthenate and 2-oleoylaminooctadecane-1,3-diol.

30. The composition of claim 1, wherein said at least one otherwise unstable compound is N-[2-[(2,6-dimethylphenyl)amino]-2-oxoethyl]-N,N-diethylbenzenemethanaminium benzoate.

31. The composition of claim 1, wherein said composition additionally comprises at least one adjuvant chosen from thixotropic agents, UVA sunscreens, UVB sunscreens, dispersants, wetting agents, dulling agents, adhesion agents, spreading agents, rheological agents, preservatives, antioxidants, thickeners and nail hardeners.

32. The composition of claim 31, wherein said UVA sunscreens and UVB sunscreens are chosen from benzophenones and ethyl 2-cyano-3,3-diphenylacrylate.

33. The composition of claim 1, wherein said composition further comprises at least one thixotropic agent.

34. The composition of claim 33, wherein said at least one thixotropic agent is chosen from stearlkenium hectorite and quaternium-18hectorite.

35. A method of decorating the nails comprising applying to said nails an effective amount of a cosmetic varnish composition of claim 1.

36. A method of treating the nails comprising applying to said nails an effective amount of a cosmetic varnish composition of claim 1.

37. A method of stabilizing a cosmetic varnish composition containing nitrocellulose and at least one otherwise unstable compound chosen from amino- and amido-functional compounds comprising the step of including in said composition at least one compound chosen from N-chlorosuccinimide and boric acid in an amount effective to stabilize said at least one otherwise unstable compound.

38. A cosmetic varnish composition comprising at least one solvent, at least one nitrocellulose, at least one plasticizer, at least one resin, at least one otherwise unstable compound, and at least one stabilizer chosen from N-chlorosuccinimide and boric acid, said at least one stabilizer being present in an amount effective to stabilize said at least one otherwise unstable compound.

* * * * *

UNITED STATES PATENT AND TRADEMARK OFFICE
CERTIFICATE OF CORRECTION

PATENT NO. : 6,203,806 B1
DATED : March 20, 2001
INVENTOR(S) : Roland Ramin et al.

Page 1 of 1

It is certified that error appears in the above-identified patent and that said Letters Patent is hereby corrected as shown below:

<u>Title page,</u>
Item [73], Assignee, "S,A." should read --S.A. --.

<u>Column 5, claim 34,</u>
Line 24, "stearlkenium" should read -- stearalkonium --.
Line 25, "quaternium-18hectorite" should read -- quaternium-18 hectorite --.

Signed and Sealed this

Fifth Day of February, 2002

Attest:

JAMES E. ROGAN
*Director of the United States Patent and Trademark Office*

*Attesting Officer*